United States Patent
Crouch et al.

(10) Patent No.: US 7,063,726 B2
(45) Date of Patent: Jun. 20, 2006

(54) PLASTICIZED BONE GRAFTS AND METHODS OF MAKING AND USING SAME

(75) Inventors: Katrina Crouch, Virginia Beach, VA (US); Lloyd Wolfinbarger, Norfolk, VA (US); Robert O'Leary, Deltaville, VA (US); Louis Ford, Virginia Beach, VA (US)

(73) Assignee: LifeNet, Virginia Beach, VA (US)

( * ) Notice: Subject to any disclaimer, the term of this patent is extended or adjusted under 35 U.S.C. 154(b) by 347 days.

(21) Appl. No.: 10/289,574

(22) Filed: Nov. 7, 2002

(65) Prior Publication Data

US 2003/0135284 A1 Jul. 17, 2003

Related U.S. Application Data

(60) Continuation-in-part of application No. 09/874,862, filed on Jun. 5, 2001, now Pat. No. 6,569,200, which is a division of application No. 09/107,459, filed on Jun. 30, 1998, now Pat. No. 6,293,970.

(51) Int. Cl.
*A61F 2/28* (2006.01)

(52) U.S. Cl. .................................. 623/23.61
(58) Field of Classification Search ............. 623/23.61
See application file for complete search history.

(56) References Cited

U.S. PATENT DOCUMENTS

| | | | |
|---|---|---|---|
| 4,278,701 A | 7/1981 | Von Hagens | |
| 4,539,716 A | 9/1985 | Bell | |
| 4,546,500 A | 10/1985 | Bell | |
| 4,776,853 A | 10/1988 | Klement et al. | |
| 4,801,299 A | 1/1989 | Brendel et al. | |
| 4,835,102 A | 5/1989 | Bell et al. | |
| 4,846,835 A | 7/1989 | Grande | |
| 4,969,912 A | 11/1990 | Kelman et al. | |
| 5,061,286 A | 10/1991 | Lyle | |
| 5,171,273 A | 12/1992 | Silver et al. | |
| 5,290,558 A | 3/1994 | O'Leary et al. | |
| 5,298,254 A | 3/1994 | Prewett et al. | |
| 5,333,626 A | 8/1994 | Morse et al. | |
| 5,336,616 A | 8/1994 | Livesey et al. | |
| 5,352,463 A | 10/1994 | Badylak et al. | |
| 5,432,712 A | 7/1995 | Chan | |
| 5,466,462 A | 11/1995 | Rosenthal et al. | |
| 5,507,813 A | 4/1996 | Dowd et al. | |
| 5,513,662 A | 5/1996 | Morse et al. | |
| 5,525,646 A | 6/1996 | Lundgren et al. | |
| 5,556,379 A | 9/1996 | Wolfinbarger | |
| 5,558,875 A | 9/1996 | Wang | |
| 5,607,476 A | 3/1997 | Prewett et al. | |
| 5,613,982 A | 3/1997 | Goldstein | |
| 5,632,778 A | 5/1997 | Goldstein | |
| 5,718,012 A | 2/1998 | Cavallaro | |
| 5,792,603 A | 8/1998 | Dunkelman et al. | |
| 5,797,871 A * | 8/1998 | Wolfinbarger, Jr. ......... 604/500 | |
| 5,820,581 A | 10/1998 | Wolfinbarger, Jr. | |
| 5,843,180 A | 12/1998 | Jaffe et al. | |
| 5,843,181 A | 12/1998 | Jaffe et al. | |
| 5,843,182 A | 12/1998 | Goldstein | |
| 5,855,617 A | 1/1999 | Orton | |
| 5,855,620 A | 1/1999 | Bishopric et al. | |
| 5,856,367 A | 1/1999 | Barrows et al. | |
| 5,863,531 A | 1/1999 | Naughten et al. | |
| 5,899,936 A | 5/1999 | Goldstein | |
| 5,899,939 A | 5/1999 | Boyce et al. | |
| 5,916,266 A | 6/1999 | Yui et al. | |
| 5,928,945 A | 7/1999 | Seliktar | |
| 5,944,755 A | 8/1999 | Stone | |
| 5,976,104 A | 11/1999 | Wolfinbarger, Jr. | |
| 5,977,034 A | 11/1999 | Wolfinbarger, Jr. | |
| 5,977,432 A | 11/1999 | Wolfinbarger, Jr. et al. | |
| 5,993,844 A | 11/1999 | Abraham et al. | |
| 5,997,896 A | 12/1999 | Carr, Jr. et al. | |
| 6,024,735 A | 2/2000 | Wolfinbarger, Jr. | |
| 6,110,206 A | 8/2000 | Stone | |
| 6,162,258 A | 12/2000 | Scarborough et al. | |
| 6,200,347 B1 | 3/2001 | Anderson et al. | |
| 6,241,771 B1 | 6/2001 | Gresser et al. | |
| 6,277,555 B1 | 8/2001 | Duran et al. | |
| 6,293,970 B1 | 9/2001 | Wolfinbarger, Jr. | |
| 6,294,041 B1 * | 9/2001 | Boyce et al. ............. 156/275.5 | |
| 6,312,474 B1 | 11/2001 | Francis et al. | |
| 6,352,708 B1 | 3/2002 | Duran et al. | |
| 6,371,992 B1 | 4/2002 | Tanagho et al. | |
| 6,376,244 B1 | 4/2002 | Atala | |
| 6,416,995 B1 | 7/2002 | Wolfinbarger, Jr. | |
| 6,428,802 B1 | 8/2002 | Atala | |
| 6,432,710 B1 | 8/2002 | Boss, Jr. et al. | |
| 6,432,712 B1 | 8/2002 | Wolfinbarger, Jr. | |
| 6,448,076 B1 | 9/2002 | Dennis et al. | |
| 6,458,158 B1 | 10/2002 | Anderson et al. | |
| 6,479,064 B1 | 11/2002 | Atala | |
| 6,544,289 B1 | 4/2003 | Wolfinbarger, Jr. et al. | |
| 6,569,200 B1 | 5/2003 | Wolfinbarger, Jr. et al. | |
| 6,630,001 B1 | 10/2003 | Duran et al. | |
| 6,734,018 B1 | 5/2004 | Wolfinbarger, Jr. | |

(Continued)

OTHER PUBLICATIONS

U.S. Appl. No. 09/698,493, Anderson et al.

(Continued)

Primary Examiner—Kevin Shaver
Assistant Examiner—Michael B. Priddy
(74) Attorney, Agent, or Firm—W. Jackson Matney, Jr.; Baker & McKenzie LLP

(57) ABSTRACT

The invention provides a plasticized bone and/or soft tissue product that does not require special conditions of storage, for example refrigeration or freezing, exhibits materials properties that approximate those properties present in natural tissue, is not brittle, does not necessitate rehydration prior to clinical implantation and is not a potential source for disease transmission. Replacement of the chemical plasticizers by water prior to implantation is not required and thus, the plasticized bone or soft tissue product can be placed directly into an implant site without significant preparation in the operating room.

28 Claims, No Drawings

U.S. PATENT DOCUMENTS

| | | | |
|---|---|---|---|
| 6,743,574 | B1 | 6/2004 | Wolfinbarger, Jr. |
| 6,783,556 | B1 | 8/2004 | Gabbay |
| 2001/0004715 | A1 | 6/2001 | Duran et al. |
| 2002/0004715 | A1 | 1/2002 | Limori |
| 2003/0083752 | A1 | 5/2003 | Wolfinbarger, Jr. et al. |
| 2003/0087428 | A1 | 5/2003 | Wolfinbarger, Jr. et al. |
| 2003/0135284 | A1 | 7/2003 | Crouch et al. |
| 2003/0217415 | A1 | 11/2003 | Crouch et al. |
| 2004/0057936 | A1 | 3/2004 | Cheung et al. |

OTHER PUBLICATIONS

Wolfinbarger, L., Zhang, Yi, Adam, BLT., Hornsi, D., Gates, K., and Sutherland, V., 1994, "Biomechanical aspects on rehydrated freeze–dried human allograft dura mater tissues" J. Applied biomaterials, 5:265–270.

H.–H. Sievers, et al., "Decellularized pulmonary homograft for reconstruction of the right ventricular outflow tract: first clinical experience" Z. Kardiol, vol. 92, No. 53, 2003.

Robert Madden, et al., "Decellularized Cadaver Vein Allografts Used for Hemodialysis Access Do Not Cause Allosensitization or Preclude Kidney Transplantation" Journal of Kidney Diseases, vol. 40, No. 6, 2002, 1240–1243.

P.M. Dohmen, et al., "In Vitro hydrodynamics of a decellularized pulmonary porcine valve, compared with a glutaraldehyde and polyurethane heart valve" Journal of Artificial Organs, vol. 25, No. 11, 2002, 1089–1094.

B.S. Conklin, et al., "Development and evaluation of a novel decellularized vascular xenograft" Medical Engineering and Physics, vol. 24, 2002, 173–183.

J. Clark, et al., "Decellularized Dermal Grafting in Cleft Palate Repair" Facial Plastic Surg., vol. 5, 2003, 40–44.

Ronald C. Elkins, et al., "Decellularized Human Valve Allografts" Society of Thoracic Surgeons, 2001, S428–432.

Steven Goldstein, et al., "Transpecies Heart Valve Transplant: Advanced Studies of a Bioengineered Xeno–Autograft" Society of Thoracic Surgeons, 2000, 1963–1969.

Pascal M. Dohmen, et al., "Ross Operation with a Tissue–Engineered Heart Valve" Society of Thoracic Surgeons, 2002, 1438–1442.

David W. Courtman, et al., "Biomechanical and ultrastructural comparison of cryopreservation and a novel cellular extraction of porcine aortic valve leaflets" Journal of Biomedical Materials Research, vol. 29, 1995, 1507–1516.

Gregory Wilson, et al., "Acellular Matrix Allograft Small Caliber Vascular Prostheses" Trans. Am. Sog. Artif. Intern. Organs, 1990, vol. XXXVI, M340–343.

David W. Courtman, et al., "The Acellular Matrix Vascular Prosthesis: Investigation of its Potential as a Xenograft for Clinical Application" Biomaterial Tissue Interfaces, vol. 10, 1992, 241–246.

David W. Courtman, et al., "Development of a pericardial acellular matrix biomaterial: Biochemical and mechanical effects of cell extraction" Journal of Biomedical Materials Research, vol. 28, 1994, 655–666.

Gregory J. Wilson, et al., "Acellular Matrix: A Biomaterials Approach for Coronary Artery Bypass and Heart Valve Replacement" Society of Thoracic Surgeons, 1995, S353–358.

Sotiris A. Korrossis, et al., "Tissue Engineering of Cardiac Valve Prostheses II: Biomechanical Characterization of Decellularized Porcine Aortic Heart Valves" Heart Valve Disease 11, 2002, 463–471.

Schwade, N., "Implants, Soft Tissue, Alloderm," emedicine.com, copyright 2004.

Kreuz, F., et al., "The Preservation and Clinical Use of Freeze Dried Bone," J Bone Joint Surg. 1951; 33A: 863.

Lalka, et al., "Acellular vascular matrix: A natural endothelial cell substrate," Annals of Vascular Surgery, vol. 3, No. 2, 1989, 108–117.

Boyne, P., Cryobiology, vol. 4, No. 6 (1968), pp. 341–357.

Pappas, A., Cryobiology, vol. 4, No. 6 (1968), pp. 358–375.

Triantafyllou et al., Acta Orthopaedica Belgica, vol. 41, Suppl. 1, (1975), pp. 35–44.

Pelker, et al., Clinical Orthopaedics and Related Research, No. 174, (Apr. 1983), pp. 54–57.

Pelker, et al., Journal of Orthopaedic Research, vol. 1, No. 4, (1984), pp. 405–411.

Pelker, et al., Orthopedic Clinics of North America, vol. 18, No. 2, (Apr. 1987), pp. 235–239.

Jerosch et al., Zeitschrift Orthopadie 132, (1994), pp. 335–341.

Voggenreiter et al., Archives of Orthopaedic and Traumatic Surgery, vol. 113, (1994), pp. 294–296.

Kang et al., Yonsei Medical Journal, vol. 36, No. 4, (1995), pp. 332–335.

Bianchi et al., $21^{st}$ Annual Meeting, American Association of Tissue Banks, (Aug. 23–27, 1997), p. 48.

Balderson et al., $45^{th}$ Annual Meeting, Orthopaedic Research Society, (Feb. 1–4, 1999), pp. 785.

* cited by examiner

PLASTICIZED BONE GRAFTS AND METHODS OF MAKING AND USING SAME

This application is a continuation-in-part application of U.S. patent application Ser. No. 09/874,862, filed on Jun. 5, 2001 now U.S. Pat. No. 6,569,200, which is a divisional application of U.S. patent application Ser. No. 09/107,459, filed on Jun. 30, 1998 now U.S. Pat. No. 6,293,970.

FIELD OF THE INVENTION

The present invention provides a plasticized dehydrated bone and/or soft tissue product that does not require special conditions of storage, for example refrigeration or freezing, exhibits materials properties that approximate those properties present in normal hydrated tissue, is not brittle and does not necessitate rehydration prior to clinical implantation. Replacement of the chemical plasticizers by water prior to implantation is not required and thus, the bone or soft tissue plasticized product can be placed directly into an implant site without significant preparation in the operating room. The present plasticized graft does not need rehydration, possesses adequate materials properties, and is not a potential source for disease transmission.

BACKGROUND OF THE INVENTION

Bone tissue is a homogeneous material including osteoid and minerals. The osteoid is a viscous gel-like material including primarily type I collagen (approximately 90%), proteoglycans, and various sulfated and non-sulfated mucopolysaccharides. The mineral component consist primarily of a crystalline form of calcium phosphate, hydroxyapatite, with amounts of calcium carbonate, tricalcium phosphate, and smaller amounts of other forms of mineral salts. This bone tissue is laid down around cells called osteocytes and these cells are found in small interconnected channels (lacunnae) which are interconnected through a series of channels including the Haversian canal system. At the level of the microscope, it is possible to observe that bone tissue is organized into osteons of compact bone made of concentric, perivascular layers of highly coaligned mineralized collagen fiber bundles. The predominant orientation within a single layer varies with respect to the vascular axis and various combinations of orientation in successive lamellae and results in variable overall collagen orientation within each osteon. Differences in overall collagen orientation are directly reflected in differing mechanical behavior of single osteons. Transversely oriented collagen results in better resistance to compressive loading along the axis, whereas predominant longitudinal orientation results in better resistance to tensile stress. The predominant orientation of collagen within a cross-section of long bone is not random, but matches the expected distribution of mechanical stress across the section, and its rotational shift along the whole shaft. More transverse collagen is deposited at sites of compressive loading, and more longitudinal collagen is deposited at sites of tensile stress. These structural oriented bone tissues in a load-bearing bone are presumed to be laid down by the osteocytes present in the bone and bone remodeling mediates mechanical adaptation in compact bone.

A bone is typically comprised of bone tissue in the form of cortical and trabecular bone. Cortical bone is frequently referred to as compact bone and is the major load-bearing part of a bone. Trabecular bone is present in what is typically referred to as cancellous bone where it appears as densely interconnected structure of "spongy" bone. Spongy bone is typically bone that contains the hemotopoietic cellular elements which is called bone marrow. Trabecular bone can be described as forming a cross-bracing lattice between cortical bone in a bone. It is important to emphasize a need to differentiate between "a bone" and "bone" (as a tissue). A bone is comprised of bone tissue present as cortical and cancellous (spongy) bone.

The mineralized osteoid typical of bone tissue is hydrated along the organic molecular structure and is an essential element of the mineral structure. Hydrating molecules of water form complex molecular associations with these organic and non-organic elements of bone tissue and can be described as being tightly bound, loosely bound, and free. Free water and loosely bound water can frequently be removed from bone tissue with only minor changes in the overall mechanical characteristics of the bone tissue. Tightly bound water can be removed only under extreme conditions and results in significant changes in the physical and mechanical properties of bone tissue. In fresh bone, water serves a solvating function in bone tissue allowing proper orientation and molecular spacing of the collagen fibrils which maintain structural alignment of the mineral phase in association with the organic phase.

Bone tissue in the form of bone grafts for implantation into a patient, is typically preserved and provided in a dehydrated state. Dehydration of bone tissue through drying, whether by air drying or sublimation as in freeze-drying, results in alteration of the molecular structure of the bone tissue and as a result of the reorientation of the collagen fibrils and the crystalline mineral phase, stress accumulates in the bone tissue. This stress can be relieved by rehydration or by the occurrence of small or large dislocations of structure. Small dislocations are designated micro fractures and are not usually visible to the naked eye. Large dislocations are designated fractures and are usually visible to the naked eye.

In a long bone, for example a femur, tibia, fibula, or humerus, the shaft separates the proximal and distal ends of the long bone. The shaft serves to focus loads applied to the whole bone into a smaller diameter than found at the proximal and distal ends of the long bone and the shaft of a long bone is typically of a cylindrical shape and is comprised of compact (cortical) bone. Loads applied along the axis of the shaft require that the cortical bone maintains a constant circumference, i.e. the tendency to failure would distort the bone tissue perpendicular to the axis of load application. Thus, the orientation of the collagen fibers should be such that tensile stress is resisted along the axis of loading and compressive stress is resisted perpendicular to loading. Drying of shaft portions of long bones results in reorientation of collagen fibers and the mineral phase such that changes in the circumferential orientation create stress within the bone matrix which can be relieved only by rehydration or occurrence of a fracture which allows a reorientation approximating the original orientation. In dehydrated cortical ring grafts cut from the shafts of long bones, this stress release can present as a fracture along the long axis of the bone shaft leaving a circumference which approximates the circumference of the cortical ring graft prior to drying. By rehydrating bone grafts prior to implantation, the potential for fracture formation which can compromise the function of the bone product can be reduced, but not eliminated. Fractures as discussed above can occur in dehydrated bone prior to rehydration and result in a graft having compromised biomechanical properties, which in turn can result in graft failure when implanted in a patient.

Load-bearing soft tissue grafts such as ligaments, tendons, and fascia lata are frequently provided in a freeze-dried state. Such grafts must be rehydrated prior to clinical implantation. Such soft tissue grafts typically contain collagen, elastin, and assorted proteoglycans and mucopolysaccharides. The collagens and elastins are the load-bearing components of these soft tissue grafts and the assorted proteoglycans and polysaccharides serve to bind the fibrillar collagens into a matrix-like structure. The structural organization of fascia lata is similar to dura mater in being isotropic in load-bearing properties (Wolfinbarger, L., Zhang, Y., Adam, BLT., Hornsi, D., Gates, K., and Sutherland, V., 1994, "Biomechanical aspects on rehydrated freeze-dried human allograft dura mater tissues" J. Applied Biomaterials, 5:265–270) whereas tendons (for example the Achilles tendon) or ligaments (for example the Anterior cruciate ligament) are typically anisotropic in load-bearing properties. In these types of load-bearing soft tissue grafts, the tensile properties of the tissues depend on the flexibility of the collagenous structures to stretch under load and return to their original dimensions upon removal of the load.

A wide variety of bone and soft tissue products are used in veterinary, medical, orthopaedic, dental, and cosmetic surgery applications. These bone and soft tissue products can be used in load-bearing and non-load bearing applications and the bone and soft tissue products can be supplied under a variety of forms. Bone products are provided as fresh-frozen, freeze-dried, rehydrated freeze-dried, air-dried, organic solvent preserved, or provided preserved by other similar types of preservation methods. Each method of preservation of bone product possesses selected advantages and disadvantages and thus the method of preservation is generally modified to select for specific needs of a given bone graft. Soft tissue products are typically provided as fresh-frozen or freeze-dried and each method of preservation of soft tissue products possess selected advantages and disadvantages and thus the method of preservation is generally modified to select for specific needs of a given soft tissue product.

Bone and soft tissue products preserved and stored by methods involving freeze-drying (removal of water by sublimation) yield a bone or soft tissue product which is significantly more brittle than normal bone or soft tissue, and has a tendency to fracture into numerous small pieces, which ultimately can result in graft failure. Specifically, freeze-drying causes grafts to be brittle and typically causes shrinkage where the shrinkage is often not uniform, thereby causing graft failure; solvent preservation using for example, acetone or alcohol, can cause irreversible denaturation of proteins, and solubilization of solvent soluble components, including for example, lipids. These alterations in materials properties of the bone and soft tissue products necessitates a rehydration step in preparation of the bone and soft tissue product for implantation. However, rehydration does not solve the problem that grafts can fracture prior to rehydration, thereby making rehydration futile, and if there are micro fractures prior to rehydration they remain after rehydration. These grafts are more likely to fail regardless of whether or not they are rehydrated. Even after rehydration the materials properties do not approximate the materials properties of normal bone.

Bone and soft tissue products are generally separated into load-bearing and non-load-bearing products. Examples of non-load bearing bone products are ground demineralized bone which are used for inducing new bone formation in a particular implant site. Load-bearing bone products are rarely demineralized and are used at implant sites where the bone graft will be expected to withstand some level of physical loads. It is therefore important that load bearing bone products not fail during normal movements of the implant recipient and that the bone products not stimulate a pronounced physiological response. The majority of bone products are provided in either the fresh-frozen or freeze-dried format. The fresh-frozen format is undesirable because it includes donor derived bone marrow and is thus immunogenic and a source of disease transmission. The freeze-dried format is less of a problem than fresh-frozen grafts in the potential for disease transmission, however a freeze-dried bone graft is significantly more brittle than normal bone, more brittle than fresh-frozen bone, and must be rehydrated prior to clinical usage.

In that clinicians typically do not have time to adequately rehydrate bone graft products in the operating room, it is advantageous to provide a plasticized bone product which does not need rehydration, possesses adequate materials properties, and is not a potential source for disease transmission.

SUMMARY OF THE INVENTION

It is an objective of the invention to provide implantable, non-demineralized, load-bearing bone products which are mechanically stabilized by use of biocompatible plasticizers.

It is a further objective of the invention to provide implantable, load-bearing, soft tissue products which are mechanically stabilized by use of biocompatible plasticizers.

It is also an objective of the invention to provide implantable, load-bearing, bone products which do not require rehydration.

It is yet a further objective of the invention to provide implantable, load-bearing, soft tissue products which do not require rehydration.

It is an objective of the invention to provide methods of plasticizing load-bearing bone and soft tissue products.

It is a further objective of the invention to provide plasticized bone and soft tissue products which are resistant to proliferation of microorganisms.

It is yet a further objective of the invention to provide bone and soft tissue products which can be stored at room temperature using conventional packaging.

It is a further objective of the invention to provide plasticized bone and soft tissue products where the plasticizer can be readily removed prior to implantation.

It is a further objective of the invention to use plasticizers to plasticize bone and soft tissue products which are not toxic to a recipient of the plasticized bone or soft tissue graft.

It is yet a further objective of the invention to provide implantable load-bearing bone and so ft tissue products which are similar in physical, chemical, and biological properties as compared to normal tissue (fresh bone or fresh soft tissues) yet lack the inherent disadvantages (including for example, potential disease transmission, increased immunogenicity, and a tissue (e.g. bone marrow) which can yield toxic degradation products and/or retard graft incorporation) of fresh-frozen, dehydrated, and freeze-dried bone and/or soft tissue products.

It is a further objective of the invention to provide a plasticized bone graft suitable for transplantation into a human, including a non-demineralized bone graft having an internal matrix essentially free from bone marrow elements; and one or more plasticizers contained in the internal matrix.

It is an object of the invention to provide a plasticized bone graft, including a cleaned, non-demineralized, bone graft; and one or more plasticizers, where the cleaned non-demineralized bone graft is impregnated with the one or more plasticizers.

It is yet a further objective of the invention to provide a plasticized bone graft, including a cleaned, non-demineralized, bone graft including one or more plasticizers.

It is a further objective of the invention to provide a method for producing a plasticized bone graft suitable for transplantation into a human, by impregnating a cleaned, non-demineralized, bone graft with one or more plasticizers to produce a plasticized bone graft.

Plasticity of soft tissues depends primarily on the waters of hydration present in the matrix structure, where water movement under a load is restricted by the viscous nature of the proteoglycan/polysaccharide component, and bound waters of hydration in the collagen component affect the flexibility of the tensile component of the tissues. The invention deals with the plasticization of these load bearing tissue constructs where the water is replaced with one or more plasticizers including for example, glycerol (glycerin USP) (liquid substitution) such that the graft does not need to be rehydrated or washed to remove the plasticizer prior to clinical implantation.

The present invention provides a plasticized bone or soft tissue product, which requires no or minimal processing just prior to implantation, by providing a plasticized bone and/or soft tissue product that exhibits materials properties that approximate those properties present in normal hydrated tissue, is not brittle and does not necessitate rehydration prior to implantation.

DETAILED DESCRIPTION

I. Definitions:

The below definitions serve to provide a clear and consistent understanding of the specification and claims, including the scope to given such terms.

Alcohol. By the term "alcohol" is intended for the purposes of the present invention, one of a series of organic chemical compounds in which a hydrogen attached to carbon is replaced by a hydroxyl. Suitable alcohols useful in the plasticizer composition of the present invention preferably include $C_1$–$C_{10}$ alcohols, and more preferably ethanol and isopropyl alcohol.

Allowash™ Solution. By the term "Allowash™ Solution" is intended those detergent compositions disclosed in U.S. Pat. No. 5,977,034, issued Nov. 2, 1999, incorporated herein by reference. Examples of suitable ALLOWASH compositions include: a cleaning composition containing about 0.06 wt % polyoxyethylene-4-lauryl ether, about 0.02 wt % poly(ethylene glycol)-p-nonyl-phenyl-ether, about 0.02 wt % octyphenol-ethyleneoxide, and endotoxin free deionized/distilled water.

Biocompatible. By the term "biocompatible" is intended for the purposes of the present invention, any material which does not provoke an adverse response in a patient. For example, a suitable biocompatible material when introduced into a patient does not itself provoke a significant immune response, and is not toxic to the patient.

Biomechanical strength. By the term "biomechanical strength" is intended for the purposes of the present invention, those properties exhibited by a tissue graft, including loading strength, compressive strength, and tensile strength.

Bone graft. By the term "bone graft" is intended for the purposes of the present invention, any bone or piece thereof or combination of pieces, obtained from a donor for example a human or animal and/or cadaver donor, including for example cortical bone and/or cancellous bone and/or cortico-cancellous bone, and including for example any essentially intact bone graft including for example any essentially intact bone graft including for example the femur, tibia, ilia, humorous, radius, ulna, ribs, whole vertebrae, mandibula and/or any bone which can be retrieved from a donor with minimal cutting of that bone for example, one half of an ulna, a femur cut in half to yield a proximal half and a distal half, femoral head, acetabula, distal femur, femur shaft, hemi-pelvi, humerus shaft, proximal femur, proximal femur with head, proximal humeri, proximal tibia, proximal tibia/plateaus, talus, tibia shaft, humeral head, ribs, and/or at least a substantial portion of a whole bone, i.e. at least one-quarter of a whole bone; and/or any cut bone grafts including for example an illiac crest wedge, a Cloward dowel, a cancellous cube, a fibular strut, cancellous block, a crock dowel, femoral candles, femoral ring, femur segment, fibula segment, fibular wedge, tibia wafer, ilium strip, Midas Rex dowel, tibial segment, and radius/ulna wedge; and/or a composite bone graft including cortical and/or cancellous and/or cortico-cancellous bone, and any combination thereof including for example as disclosed in U.S. patent application Ser. Nos. 09/699,029 and 09/698,493, and U.S. Pat. No. 6,200,347, all incorporated herein by reference in their entirety.

Bone marrow elements. By the term "bone marrow elements" is intended for the purposes of the present invention, the highly cellular hematopoietic connective tissue filling the medullary cavities and spongy epiphysis of bones which may harbor bacterial and/or viral particles and/or fungal particles, and includes for example, blood and lipid.

Cleaned bone graft. By the term "cleaned bone graft" is intended for the purposes of the present invention, a bone graft that has been processed for example, using means know in the art, to remove bone marrow elements.

Dehydrated bone or soft tissue. By the term "dehydrated bone or soft tissue" is intended bone tissue or soft tissue which is preserved by dehydration, where dehydration includes replacement of water by a plasticizer and/or removal of water from a tissue by one or more drying methods including for example, freeze-drying, and/or sublimation and/or air drying and/or liquid substitution.

Essentially free from. By the term "essentially free from" is intended for the purposes of the present invention, a bone graft where the material removed (i.e., bone marrow elements) from the bone graft is not detectable using detection means known in the art at the time of filing of this application.

Incubating. By the term "incubating" is intended for the purposed of the present invention, processing a bone graft in for example, a plasticizer composition by soaking the graft in the composition, shaking the graft with the composition, subjecting the graft to flow of the composition where the flow is induced by negative or positive pressure, subjecting the graft and/or the composition to negative or positive pressure, soaking the bone graft in a plasticizer composition in a negative pressure environment, sonicating the graft with one or more plasticizer compositions, or centrifuging the graft with one or more plasticizer composition.

Impregnating. By the term "impregnating" is intended for the purposes of the present invention, any processing conditions which result in filling the internal matrix of a bone graft with a plasticizer composition.

Internal matrix. By the term "internal matrix" is intended for the purposes of the present invention, the spongy epiphysis of bones, the intercellular substance of bone tissue including collagen fibers and inorganic bone salts; or in soft tissue, the intercellular substance of such soft tissue including for example ligaments and tendons, including collagen and elastin fibers and base matrix substances.

Load-bearing. By the term "load-bearing" is intended for the purposes of the present invention a non-demineralized bone product or soft tissue product for implantation in a patient at a site where the bone graft or soft tissue graft will be expected to withstand some level of physical loads Materials properties. By the term "materials properties" is intended for the purposes of the present invention, those properties present in normal fresh bone which include for example, loading strength, compressive strength, tensile strength, and deformability.

Negative pressure. By the term "negative pressure" is intended for the purposes of the present invention, a pressure below atmospheric pressure, i.e. below 1 atm.

Natural or normal bone or soft tissue. By the term "normal bone or soft tissue" or "natural bone or soft tissue" is intended for the purposes of the present invention, fresh hydrated autogenous and/or fresh-frozen hydrated allograft tissue including for example, bone, fascia, ligaments, and tendons.

Permeation enhancer. By the term "permeation enhancer" is intended for the purposes of the present invention, any agent including for example, isopropyl alcohol, surfactants, detergents and alcohols, that facilitates penetration of the one or more plasticizers or plasticizer composition into the bone or soft tissue. Permeation is enhanced due to the reduced surface tension of the aqueous solution.

Plasticization. By the term "plasticization" is intended for the purposes of the present invention, replacing free and loosely bound waters of hydration in a tissue with one or more plasticizers without altering the orientation of the collagen fibers and associated mineral phase.

Plasticizer. By the term "plasticizer" is intended for the purposes of the present invention, any biocompatible compounds which are soluble in water and can easily displace/replace water at the molecular level and preferably have a low molecular weight such that the plasticizer fits into the spaces available to water within the hydrated molecular structure of the bone or soft tissue. Such plasticizers are preferably not toxic to the cellular elements of tissue into which the graft is to be placed, or alternatively, the plasticizer is easily removed from the graft product prior to implantation. Suitable plasticizers are preferably compatible with and preferably readily associates with the molecular elements of the bone tissue and/or soft tissue. Suitable plasticizers include for example: glycerol (glycerin USP), adonitol, sorbitol, ribitol, galactitol, D-galactose, 1,3-dihydroxypropanol, ethylene glycol, triethylene glycol, propylene glycol, glucose, sucrose, mannitol, xylitol, mesoerythritol, adipic acid, proline, hydroxyproline or similar water-soluble small molecular weight solutes which can be expected to replace water in the base matrix structure of bone tissue and/or soft tissue and provide the hydrating functions of water in that tissue. Suitable solvents include for example: water, alcohols, including for example ethanol and isopropyl alcohol.

Plasticizer composition. By the term "plasticizer composition" is intended for the purposes of the present invention, any composition which includes one or more plasticizers and one or more biocompatible solvents. Suitable solvents include for example: water, and alcohols, including for example: $C_1$–$C_{10}$ alcohols, and more preferably ethanol and isopropyl alcohol.

Positive pressure. By the term "positive pressure" is intended for the purposes of the present invention, a pressure above atmospheric pressure, i.e. above 1 atm.

Rehydration. By the term "rehydration" is intended for the purposes of the present invention, hydrating a dehydrated plasticized tissue graft or a dehydrated non-plasticized tissue graft, with water, for example, prior to implantation into a patient. In the case of a plasticized graft, the plasticizer may optionally be not replaced by water or may optionally be partially or fully replaced by water.

Soft tissue grafts. By the term "soft tissue grafts" is intended for the purposes of the present invention, soft tissue exclusive of bone, including connective tissue including ligaments and tendons, skin, vascular tissue including arteries and veins, pericardium, dura mater, fascia, heart valves, urethra, umbilical cord, and nerves. Soft tissue grafts are composed of an internal matrix which includes collagen, elastin and high molecular weight solutes where during cleaning cellular elements and small molecular weight solutes are removed.

II. Plasticizers

Plasticization of load-bearing bone or soft tissue grafts represents a method of replacing free and loosely bound waters of hydration in the tissue with a plasticizer composition containing one or more plasticizers, without altering the orientation of the collagen fibers and associated mineral phase. Suitable plasticizers include compounds which are soluble in water and can displace/replace water at the molecular level. Suitable plasticizers preferably have a low molecular weight such that the plasticizer fits into the spaces available to water within the hydrated molecular structure of the bone or soft tissue. Such plasticizers are not toxic to the cellular elements of tissue into which the graft is to be placed, or alternatively, the plasticizer is easily removed from the graft product prior to implantation. Finally, the plasticizer is preferably compatible with and preferably readily associates with the molecular elements of the bone or soft tissue.

Plasticizers suitable for use in the present invention include for example, a variety of biocompatible aqueous solutions. Examples of acceptable plasticizers include, but are not restricted to, members of the polyol family (sugar alcohols) of compounds including $C_2$–$C_7$ polyols, monoglycerides (such as monoolein and monolinolein), and various short- and medium-chain free fatty acids (such short-chain free fatty acids preferably having a carbon chain length of less than six ($C_6$); and such medium-chain free fatty acids preferably having a carbon chain length of from $C_{12}$–$C_{14}$) and their corresponding monacylglycerol esters (Mgs) such as the saturated Mgs, ranging in carbon chain length $C_5$–$C_{16}$, and preferably $C_5$–$C_{14}$ Mgs. Specific plasticizers include, but are not limited to, glycerol (glycerin USP), adonitol, sorbitol, ribitol, galactitol, D-galactose, 1,3-dihydroxypropanol, ethylene glycol, triethylene glycol, propylene glycol, glucose, sucrose, mannitol, xylitol, mesoerythritol, adipic acid, proline, hydroxyproline or similar water-soluble small molecular weight solutes which can be expected to replace water in the matrix structure of bone or soft tissue, and provide the hydrating functions of water in that tissue. Other plasticizers suitable for use in the present invention can be readily selected and employed by one of ordinary skill in the art to which the present invention pertains without undue experimentation depending on the desired clinical outcome, sensitivity of the implantation procedure, patient sensitivities, and physician choice.

The present plasticizers are preferably employed at concentrations in the range of from about 10% to 100% by weight or volume, preferably from about 50% v/v to about 100% v/v. The plasticizer can be introduced into the bone or soft tissue matrix at any number of steps in the processing procedures and at a variety of concentrations with and/or without the use of permeation enhancers. The results of plasticization of bone and soft tissue products are bone or soft tissue products which are not subject to fractures or micro fractures (as in the case of traditional dehydrated graft products), yet do not need to be rehydrated prior to use. The mechanical and use properties of a plasticized bone or soft tissue product are similar to those of natural (fresh autogenous and/or fresh-frozen allograft) bone or soft tissue.

III. Graft Cleaning and Processing

The present plasticizers may be introduced to the bone or soft tissue products at several points in the processing procedures. Bone processing and cleaning procedures suitable for use with the invention include known process, as well as the processes described in U.S. Pat. Nos. 5,556,379; 5,797,871; 5,820,581; 5,977,034; 5,976,104; 5,977,432; and 6,200,347; all hereby incorporated herein in their entirety. The plasticizers may be incorporated into the processing procedures using steps where the plasticizers are present at concentrations up to and including 100% v/v with or without permeation enhancers.

Bone tissue is cleaned and processed as described in the above-referenced patents, by for example, transection of an essentially intact bone or perforation of an essentially intact bone with attachment of sterile plastic tubing to the cut end of a transected bone or to an attachment port inserted into the perforation of the perforated bone. The bone is immersed in a cleaning solution, such solutions including known cleansing agents as well as those described in the above-referenced patents, with or without the use of for example sonication and/or centrifugation. The cleaning solution is induced to flow into, through, and out of the bone through use of a peristaltic pump or negative pressure applied to the cleaning solution. The induced flow of cleaning solution draws the bone marrow from the interior of the bone, and particularly from the cancellous bone marrow space, where it can be safely deposited in a receiving container containing a strong virucidal agent such as sodium hypochlorite (common bleach). The cleaned bone can then be further cleaned by causing the cleaning solution to be replaced with a solution of one or more decontaminating agents, including for example 3% hydrogen peroxide, with or without plasticizer. Hydrogen peroxide which in addition to its mild disinfection activity generates oxygen bubbles that can further assist in dislodging residual bone marrow materials causing the residual bone marrow material to flow from the bone and into the receiving container.

In the above-described process, after processing with the cleaning solution, after processing with a decontaminating agent, in place of processing with a decontaminating agent, or after dehydration, the cleaned graft is plasticized for example, by processing the cleaned graft with a plasticizer composition containing one or more plasticizers including for example glycerin USP in a solvent.

IV. Plasticization

Bone and soft tissue grafts can be cleaned and processed using conventional methods or those described in U.S. Pat. Nos. 5,556,379; 5,797,871; 5,820,581; 5,977,034; 5,976,104; 5,977,432; and 6,200,347. When processing using these methods the graft is plasticized by adding one or more plasticizers or one or more plasticizer compositions to processing steps after bone cleaning is essentially completed. The one or more plasticizers are added to fully hydrated bone tissue, and the plasticizers are induced to penetrate into the bone tissue optionally using a permeation enhancer. Thus, the bone or soft tissue is plasticized yet the materials properties of the tissue is similar to the materials properties of normal tissue, i.e. hydrated bone or soft tissue. The produced plasticized bone or soft tissue graft contains minimal quantities of the plasticizers, can be removed from the package and directly implanted into a patient without rehydration. If the presence of these small quantities of glycerol is of concern, the bone or soft tissue grafts maybe quickly rinsed and/or washed in sterile saline just prior to implantation.

Bone or soft tissue that has been cleaned and/or processed, may be plasticized by processing with one or more plasticizer compositions containing one or more plasticizers, including for example, glycerin USP, in a solvent by for example drawing the plasticizer composition into the bone. Suitable solvents include for example, isopropyl alcohol. The alcohol/plasticizer composition can be prepared by diluting absolute (100%) isopropyl alcohol with the one or more plasticizers, including for example glycerin USP such that the plasticizer accounts for from about 50% to 100% v/v, preferably from about 60% to 100% v/v, more preferably about 80% v/v, of the total volume, and isopropyl alcohol accounts for from about 50% to 0% v/v, preferably from about 40% to 0% v/v, more preferably from about 20% v/v, of the total volume. Under this method, the original processing procedures as described in U.S. Pat. No. 5,556,379 regarding the use of 70% isopropyl alcohol, can be followed. The isopropyl alcohol facilitates penetration of the glycerol into the tissue by acting as a permeation enhancer and the glycerol more readily penetrates the tissue due to the reduced surface tension of the alcoholic solution. The induced flow of glycerol/isopropyl alcohol into, through, and out of for example, the essentially intact bone, further serves to remove residual cellular elements, for example bone marrow materials, if any. It also allows penetration of the glycerol/isopropyl alcohol solution into the most remote areas of the tissue, and facilitates a uniform distribution of the glycerol into the tissue. If desired, plasticized cancellous bone grafts may optionally be dry spun to remove any excess plasticizer present. Plasticized cortical bone grafts may optionally be blotted to remove any excess plasticizer present. The cleaned and plasticized tissue can then be packaged and stored at room temperature or under refrigeration.

Alternatively, bone or soft tissue grafts maybe plasticized after cleaning and freeze-drying. For example, tissue can be processed and cleaned according to any method including known methods, or as described in the references incorporated herein. After removal of bone marrow and/or cellular components, the tissue can be processed for example by freeze-drying. Freeze-dried or dehydrated tissue grafts preferably contain less than about 5% residual moisture, satisfying the definition of freeze-dried bone allografts as prescribed under Standards of the American Association of Tissue Banks.

Clean freeze-dried or dehydrated bone or soft tissue grafts are plasticized by processing the tissue graft with a plasticizer composition, suitable compositions including for example 20% isopropyl alcohol/80% glycerin USP or 100% glycerin USP. The alcohol/plasticizer composition can be prepared by diluting absolute (100%) isopropyl alcohol with the one or more plasticizers, including for example glycerin USP such that the plasticizer accounts for from about 50% to 100% v/v, preferably from about 60% to 100% v/v, more preferably about 80% v/v, of the total volume, and isopropyl alcohol accounts for from about 50% to 0% v/v, preferably from about 40% to 0% v/v, more preferably from about 20% v/v, of the total volume.

Due to the presence of air in the cancellous and cortical bone spaces, the plasticizers may only penetrate into the bone tissue with which it is in physical contact. Suitable methods for achieving physical contact between the plasticizer and bone or soft tissue include those methods known to one of ordinary skill in the art to which the present invention pertains. The plasticizer composition can be induced to flow into the cancellous and cortical bone spaces of bone tissue, or soft tissue, thus achieving physical contact, by various known methods that can be readily selected and employed by one of ordinary skill in the art to which the present invention pertains without undue experimentation, and include for example, agitation of the tissue with the plasticizer composition, application of a vacuum (10 to 50 mBarr) above the plasticizer. Other methods of achieving physical contact include centrifuging the bone or soft tissue graft with the plasticizer composition, for example centrifugation at about 2000–3000 rpm, more preferably about 2600 rpm, for about 30 min. to about 5 hrs. The vacuum induces the air trapped in the, for example, cancellous and cortical bone spaces/tissue to move out. The plasticizer quickly moves into the spaces previously occupied by air greatly enhancing penetration of the plasticizer into the bone or soft tissue. The plasticizer fills the spaces previously occupied by the free and bound water restoring the tissue to a materials property similar to that materials property of the original natural tissue.

The present one or more plasticizers may be introduced to soft tissue products at several points in the processing procedures, but are preferably introduced prior to the freeze-drying or dehydrating step. By introducing plasticizers prior to freeze-drying or dehydrating, the derived plasticized soft tissue graft does not need to be freeze-dried, and can be packaged and stored at room temperature, and can be implanted without rehydration/reconstitution.

Prior to packaging, excess glycerol may optionally be removed from the plasticized bone or soft tissue graft using for example, the method described in U.S. Pat. No. 5,977,432. Specifically, in the case of cancellous bone grafts, the plasticized grafts are placed into a centrifuge vessel or container and on top of inserts designed to keep the bone grafts off of the bottom of the containers. The grafts are then centrifuged at 2,500 to 4,500 rpm, preferably about 2,600 rpm, for from about 10 sec. to 3 minutes, preferably 1 minute or less. The excess glycerol or similar plasticizer exits the grafts and collects in the bottom of the centrifuge containers away from the grafts.

The plasticized grafts may then be packaged directly or packaged in a packaging format which permits application of a vacuum to the container. The later packaging format is preferably because it permits storage of grafts under vacuum and allows the ability to predict possible loss of sterility with loss of vacuum to the packaging. Preferably, the grafts are vacuum packed in peal-packs and stored at room temperature or under refrigeration.

V. Transplantation Into a Patient

Clinical usage of plasticized bone or soft tissue grafts includes direct implantation of the grafts without further processing following removal from the packaging, implantation following a brief washing in sterile isotonic saline to remove any remaining traces of plasticizer associated with the immediate surfaces of the grafts, or by implantation following an extended (approximately one hour) washing with sterile isotonic saline to remove as much plasticizer as possible. Under any of the above described further processing of grafts, the materials properties of the plasticized grafts resemble those materials properties of fully or partially hydrated natural tissue (i.e. normal bone or soft tissue). The produced plasticized graft does not need to be rehydrated prior to clinical implantation, and the graft retains the strength and compressive/tensile properties of natural tissue. Plasticized soft tissue grafts where the plasticizer is used to stabilize the matrix and load bearing components of the soft tissue graft, can also be directly implanted in a patient without rehydration/reconstitution.

Suitable surgical methods for implanting bone and soft tissue grafts into a patient are well known to those of ordinary skill in the art to which the invention pertains, and such methods are equally applicable to implantation of the present plasticized grafts. Those of ordinary skill in the art to which the present invention pertains can readily determine, select and employ suitable surgical methods without undue experimentation.

Further details of the process of the invention are presented in the examples that follow.

EXAMPLES

Example 1

Processing of a Frozen Distal Femur

A. Cleaning and Processing: A frozen distal femur is selected and all of the soft tissue and periosteum is removed. The graft is then transected to the desired length using a STRYKER saw or a band saw. Each bisected piece is not more than 30 cm in length and is straight and contains no bone fragments. The surface cartilage is then removed from the femoral condyle with wither a scalpel blade, periosteal elevator, or osteotome. The processing instructions dictate leaving the cartilage "on" when appropriate. Using a ⅜" drill bit, the cut end of the shaft is drilled approximately 5 cm. The interior of the intramedullary canal is then throughly washed with a lavage system.

An intercalary fitting is then inserted by screwing the threaded, tapered end into the cut end of the graft. The vacuum tubing is assembled by securing one end of the tubing to the nipple end of the intercalary fitting. The other end of the tubing is secured tot he piston driven pump. Finally, another section of vacuum tubing is secured to the other side of the piston pump. Approximately 4000 cc of a 1:100 dilution of ALLOWASH solution is poured into the sterile flushing vessel. The ALLOWASH solution is prepared by adding 4 cc of cleaning reagent to 3996 cc of sterile water. The flushing vessel is labeled "ALLOWASH solution." The open end of the second piece of vacuum tubing is placed into a graduated flask. The piston pump is set to "reverse" and the flow rate controller is set to 50%. The pump is turned on and at least 500 cc of the first solvent (ALLOWASH solution) is drawn to waste. Thereafter, the open end of the second piece of vacuum tubing is removed from the graduated flask and placed into the sterile flushing vessel. The drive is maintained in the "reverse" position at 50%. The ALLOWASH solution recirculates for a minimum of 15 minutes.

The 1:100 dilution of ALLOWASH solution is then decanted and approximately 4 liters of 3% hydrogen peroxide is added to the flushing vessel. The piston pump is set to reverse and the flow rate controller is set to 50%. The pump is then turned on and at least 500 cc of the 3% hydrogen peroxide solution is drawn to waste. Thereafter, the open end of the second piece of vacuum tubing is removed from the graduated flask and placed into the sterile flushing vessel. The drive is maintained in the reverse position at 50%. The hydrogen peroxide is then allowed to recirculate for a minimum of 15 minutes.

The hydrogen peroxide is then decanted and approximately 3980 cc of sterile water is added along with the entire contents of reconstituted vials of Bacitracin and Polymyxin B to the flushing vessel. The flushing vessel is clearly labeled "antibiotic." The piston pump is then set to reverse and the flow rate controller is set at 50%. The pump is turned on and at least 500 cc of antibiotic solution is drawn to waste. The open end of the second piece of vacuum tubing is removed from the graduated flask and placed into the sterile flushing vessel. The drive is maintained in the reverse position at 50%. The antibiotic solution is allowed to recirculate for a minimum of 15 minutes.

B. Plasticization: The antibiotic solution is then decanted and approximately 4 liters of 70% isopropyl alcohol/30% glycerin USP is added to the flushing vessel. The flushing vessel is clearly labeled as 70% IPA/30% glycerin USP. The piston pump is set to reverse and the flow rate controller is set to 50%. The pump is turned on and at least 500 cc of IPA/glycerin USP solution is drawn to waste.

The open end of the second piece of vacuum tubing is removed from the graduated flask and placed into the sterile flushing vessel. The drive is maintained in the reverse position and the flow controller is set at 50%. The IPA/glycerin USP solution is allowed to recirculate for a minimum of 30 minutes and is then decanted. Thereafter, 4 liters of 30% glycerin USP in sterile water is added to the flushing vessel. The flushing vessel is labeled as glycerin USP washing solution. The piston pump is set to reverse and the flow rate controller is set to 50%. The pump is turned on and at least 500 cc of washing solution is drawn to waste.

The open end of the second piece of vacuum tubing is removed from the graduated flask and placed into the sterile flushing vessel. The drive is maintained in the reverse position and the flow rate controller is set to 50%. The washing solution is allowed to recirculate for a minimum of 15 minutes. Thereafter, the bone graft is removed from the flushing vessel and processed for freeze-drying as per standard operating procedure.

Example 2

Processing of a Frozen Distal Femur

A. Cleaning and Processing: A frozen distal femur is selected and all of the soft tissue and periosteum is removed using sharp dissection techniques and periosteal elevators. The graft is then transected to the desired length using a STRYKER saw or band saw. Each bisected piece is not more than 30 cm in length and is straight and contains no bone fragments. The surface cartilage is then removed from the femoral condyle with either a scalple blade, periosteal elevator, or osteotome. The processing instructions dictate leaving the cartilage "on" when appropriate. Using a ⅜" drill bit, the cut end of the shaft is drilled approximately 5 cm. The interior of the intramedullary canal is then throughly washed with the lavage system.

An intercalary fitting is then inserted by screwing the threaded, tapered end into the cut end of the graft. The vacuum tubing is assembled by securing one end of the tubing to the nipple end of the intercalary fitting. The other end of the tubing is secured tot he piston driven pump. Finally, another section of vacuum tubing is secured to the other side of the piston pump. Approximately 4000 cc of a 1:100 dilution of ALLOWASH solution is poured into the sterile flushing vessel. The ALLOWASH solution is prepared by adding 4 cc of cleaning reagent to 3996 cc of sterile water. The flushing vessel is labeled "ALLOWASH solution." The open end of the second piece of vacuum tubing is placed into a graduated flask. The piston pump is set to "reverse" and the flow rate controller is set to 50%. The pump is turned on and at least 500 cc of the first solvent (ALLOWASH solution) is drawn to waste. Thereafter, the open end of the second piece of vacuum tubing is removed from the graduated flask and placed into the sterile flushing vessel. The drive is maintained in the "reverse" position at 50%. The ALLOWASH solution recirculates for a minimum of 15 minutes.

B. Plasticization: The 1:100 dilution of ALLOWASH solution is then decanted and approximately 4 liters of 3% hydrogen peroxide/30% glycerin USP is added to the flushing vessel. The piston pump is set to reverse and the flow rate controller is set to 50%. The pump is then turned on and at least 500 cc of the 3% hydrogen peroxide/glycerin USP solution is drawn to waste. Thereafter, the open end of the second piece of vacuum tubing is removed from the graduated flask and placed into the sterile flushing vessel. The drive is maintained in the reverse position. The hydrogen peroxide/glycerin USP is then allowed to recirculate for a minimum of 15 minutes.

The hydrogen peroxide/glycerin USP is then decanted and approximately 3980 cc of sterile water is added along with the entire contents of reconstituted vials of Bacitracin and Polymyxin B prepared in a water solution of 30% glycerin USP, to the flushing vessel. The flushing vessel is clearly labeled "antibiotic." The piston pump is then set to reverse and the flow rate controller is set at 50%. The pump is turned on and at least 500 cc of antibiotic solution is drawn to waste. The open end of the second piece of vacuum tubing is removed from the graduated flask and placed into the sterile flushing vessel. The drive is maintained in the reverse position at 50%. The antibiotic solution is allowed to recirculate for a minimum of 15 minutes.

The antibiotic solution is then decanted and approximately 4 liters of 70% isopropyl alcohol/30% glycerin USP is added to the flushing vessel. The flushing vessel is clearly labeled as 70% IPA/30% glycerin USP. The piston pump is set to reverse and the flow rate controller is set to 50%. The pump is turned on and at least 500 cc of IPA/glycerin USP solution is drawn to waste.

The open end of the second piece of vacuum tubing is removed from the graduated flask and placed into the sterile flushing vessel. The drive is maintained in the reverse position and the flow controller is set at 50%. The IPA/glycerin USP solution is allowed to recirculate for a minimum of 30 minutes and is then decanted. Thereafter, 4 liters of 30% glycerin USP in sterile water is added to the flushing vessel. The flushing vessel is labeled as glycerin USP washing solution. The piston pump is set to reverse and the flow rate controller is set to 50%. The pump is turned on and at least 500 cc of washing solution is drawn to waste.

The open end of the second piece of vacuum tubing is removed from the graduated flask and placed into the sterile flushing vessel. The drive is maintained in the reverse position and the flow rate controller is set to 50%. The washing solution is allowed to recirculate for a minimum of 15 minutes. Thereafter, the bone graft is removed from the flushing vessel and processed for freeze-drying as per standard operating procedure.

Example 3

Processing Cloward Dowels

A. Cleaning and Processing: Graft material is selected and all of the soft tissue and periosteum is removed from the distal femur, proximal and distal tibia, and cartilage is removed from the site. The femur is transected 10–15 cm above the femoral candles and the distal femoral candles are bisected. The proximal tibia is transected 10–15 cm below the tibial plateau. The distal femur or proxmal tibia is placed in a PAN-A-VISE. This is accomplished by removing a section of the diaphysis, allowing the vise jaws to grip the tissue securely. The Cloward set (12, 14, 16, 18, or 20 mm) is then assembled: 1. place the extractor assembly within the cutter shaft; 2. screw the cutter assembly onto the shaft with the aid of the Cloward set wrench; 3. screw the set-point onto the extractor assembly; and 4. insert the shaft of the Cloward set into the ⅜" variable speed drill and tighten the chuck with the key. The set-point is then placed and locked at the forward aspect of the cutter.

The apparatus is then placed on the tissue to be fashioned. Drilling is commenced at a moderate speed. After the set-point has made a deep cut in the tissue, and the teeth have begun to cut into the tissue, drilling is stopped, and the set-point apparatus is unlocked. Drilling is continued using the marks created as a guide.

The Clowards are then removed from the tissue block. A STRYKER saw or a band saw is then used to remove the cut grafts after all have been cut. Any cartilage is then trimmed from the cortical face of the Clowards using a scalpel and a #10 blade. The distal end of the graft is then trimmed perpendicular to the body of the graft with a saw making sure the fashioned graft is at least 15 mm long. The Clowards are cleansed using pulsatile water lavage. If the surface marrow is not easily removed, dry spin the grafts at 2600 rpm for 3 minutes. The grafts may optionally be further processed according to methods for example, as described in U.S. Pat. Nos. 5,797,871 and 5,977,432.

B. Plasticization: The Clowards are then placed in a sterile container with hydrogen peroxide (3%) and glycerin USP (30%) at 37–44° C. The container is sealed and the container is placed into the centrifuge. The centrifuge is then balanced. The grafts are then centrifuged at 2600 rpm for 15 minutes. The tissue is removed from the centrifuge and the grafts are placed into an ultrasonic cleaner. Equal volumes of ALLOWASH solution, hydrogen peroxide (3%), 30% glycerin USP, and antibiotics are added tot he ultrasonic cleaner and the tissue is sonicated at 37–44° C. for a minimum of 1 hour. Thereafter, the tissue is removed from the ultrasonic cleaner.

The mixture is decanted and a sterile glass container is filled with fresh 3% hydrogen peroxide/30% glycerin USP. The grafts are then placed in the container, the top is sealed and the container is taken to the large ultrasonic cleaner. The grafts are then sonicated for 90 minutes. Thereafter, the grafts are incubated overnight at 37–44° C. (a minimum of 6 hours, preferably 12–18 hours).

After incubation, the hydrogen peroxide is decanted and the basin is filled with 70% isopropyl alcohol/30% glycerin USP and the grafts are incubated at room temperature for a minimum of 30 minutes. Thereafter, the isopropyl alcohol/glycerin USP solution is decanted and the container is filled with warm 30% glycerin USP in water. The grafts are incubated for a minimum of 30 minutes. Methods of incubation include for example, soaking, sonication, mild agitation, and centrifugation.

The glycerin solution is then decanted and the Cloward dowels are removed from the container. The Cloward dowels are then placed into a sterile container. The container is sealed and placed into the centrifuge. The centrifuge is balanced and the grafts are centrifuged for 3–5 minutes to dry, and the remaining solution is removed.

The width and length of the Clowards are measured, graft identification numbers are assigned, and the information is recorded on the "Tissue Processing Log Worksheet." One graft is then placed into a glass, 120 cc bottle and the printed label is affixed with the unique numeric designator. This step is repeated until all deposits are bottled. The bottled grafts are either frozen and packaged, or frozen and freeze-dried and packaged.

Example 6

Processing Cloward Dowels

A. Cleaning and Processing. Graft material is selected and all of the soft tissue and periosteum is removed from the distal femur, proximal and distal tibia, and cartilage is removed from the site. The femur is transected 10–15 cm above the femoral candles and the distal femoral candles are bisected. The proximal tibia is transected 10–15 cm below the tibial plateau. The distal femur or proxmal tibia is placed in a PAN-A-VISE. This is accomplished by removing a section of the diaphysis, allowing the vise jaws to grip the tissue securely. The Cloward set (12, 14, 16, 18, or 20 mm) is then assembled: 1. place the extractor assembly within the cutter shaft; 2. screw the cutter assembly onto the shaft with the aid of the Cloward set wrench; 3. screw the set-point onto the extractor assembly; and 4. insert the shaft of the Cloward set into the ⅜" variable speed drill and tighten the chuck with the key. The set-point is then placed and locked at the forward aspect of the cutter.

The apparatus is then placed on the tissue to be fashioned. Drilling is commenced at a moderate speed. After the set-point has made a deep cut in the tissue, and the teeth have begun to cut into the tissue, drilling is stopped, and the set-point apparatus is unlocked. Drilling is continued using the marks created as a guide.

The Clowards are then removed from the tissue block. A STRYKER saw or a band saw is then used to remove the cut grafts after all have been cut. Any cartilage is then trimmed from the cortical face of the Clowards using a scalpel and a #10 blade. The distal end of the graft is then trimmed perpendicular to the body of the graft with a saw making sure the fashioned graft is at least 15 mm long. The Clowards are cleansed using pulsatile water lavage. If the surface marrow is not easily removed, dry spin the grafts at 2600 rpm for 3 minutes. The grafts may optionally be further processed according to methods for example, as described in U.S. Pat. Nos. 5,797,871 and 5,977,432.

The Clowards are then placed in a sterile container with hydrogen peroxide (3%) at 37–44° C. The container is sealed and the container is placed into the centrifuge. The centrifuge is then balanced. The grafts are centrifuged at 2600 rmp for 15 minutes. The tissue is removed from the centrifuge and the grafts are placed into an ultrasonic cleaner., Equal volumes of ALLOWASH solution, hydrogen peroxide (3%), and antibiotics are added to the ultrasonic cleaner and the tissue is sonicated at 37–44° C. for a minimum of 1 hour. Thereafter, the tissue is removed from the ultrasonic cleaner.

The mixture is decanted and a sterile glass container is filled with fresh 3% hydrogen peroxide. The grafts are then placed in the container, the top is sealed and the container is taken to the large ultrasonic cleaner. The grafts are then sonicated for 90 minutes. Thereafter, the grafts are incubated overnight at 37–44° C. (minimum of 6 hours, preferably 12 to 18 hours).

After incubation, the hydrogen peroxide is decanted and the basin is filled with 70% isopropyl alcohol and the grafts are incubated at room temperature for a minimum of 30 minutes. Thereafter, the isopropyl alcohol and the grafts are incubated at room temperature for a minimum of 30 minutes. Thereafter, the isopropyl alcohol is decanted and the container is filled with warm sterile water. The grafts are incubated for a minimum of 30 minutes. Methods of incubation include for example, soaking, mild agitation, sonication, and centrifugation.

The wash solution is then decanted and the Cloward dowels are removed from the container. The Cloward dowels are then placed into a sterile container. The container is sealed and placed into the centrifuge. The centrifuge is balanced. The grafts are then centrifuged for 3–5 minutes to dry and the remaining solution is removed.

The width and length of the Cloward dowels are measured, graft identification numbers are assigned, and the information is recorded on the "Tissue Processing Log Worksheet." One graft is then placed into a glass, 120 cc bottle and the printed label is affixed with the unique numeric designator. This step is repeated until all deposits are bottled. The bottled grafts are either frozen and packaged, or frozen and freeze-dried and packaged.

B. Plasticization: Viscous glycerol is then added to each bottle sufficient to cover the graft and vacuum (10 to 500 mTorr) is applied to each bottle until the air ceases to exit the grafts (usually 5–20 minutes depending on graft type). The grafts are then removed from the bottles and placed into a centrifuge container. The grafts are centrifuged for 15–30 minutes or until glycerol ceases to exit the grafts and accumulates in the space below the grafts. The bottled grafts are either packaged or placed under vacuum and packaged.

Example 7

Processing of a VG2 Cervical Grafts

A. Cleaning and Processing: VG2 cervical composite cortical bone grafts were cut, assembled and cleaned.

B. Plasticization: The cleaned grafts were dry and placed into a container with 80% v/v glycerol at room temperature. The grafts were completely covered with glycerol/alcohol. The containers were then sealed ans placed in a centrifuge. The centrifuge was balanced and the grafts were then centrifuged at 2,600 rpm for 2–5 hours. The containers were removed from the centrifuge and excess glycerol was poured off. The grafts were removed to a new container and blotted dry or dry spun at 2600 rpm for 10 seconds. The grafts were then vacuum packed and stored at room temperature.

All of the publications and patent applications cited herein are herein are hereby incorporated by reference into the present disclosure. It will appreciated by those skilled in the art that various modifications can be made without departing form the essential nature thereof. It is intended to encompass all such modifications within the scope of the appended claims.

We claim:

1. A method for producing a plasticized, load-bearing, bone graft, comprising:
   incubating a cleaned, non-demineralized, load-bearing, bone graft with one or more plasticizer compositions comprising one or more plasticizers and one or more biocompatible solvents without altering orientation of collagen fibers.

2. The method of claim 1, said cleaned, non-demineralized, load-bearing, bone graft is essentially free from bone marrow elements.

3. The method of claim 1, said one or more biocompatible solvents comprise one or more alcohols.

4. The method of claim 3, said plasticizer is glycerol and said one or more alcohols is isopropyl alcohol.

5. The method of claim 1, said one or more plasticizers are present in said plasticizer composition at a concentration of from about 50% v/v to about 100% v/v and said one or more biocompatible solvents are present in said plasticizer composition at a concentration of from about 50% v/v to about 0% v/v.

6. The method of claim 4, said glycerol is present at about 80% v/v and said isopropyl alcohol is present at about 20% v/v.

7. The method of claim 5, said one or more plasticizers are present in said plasticizer composition at a concentration of from about 60% v/v to about 90% v/v and said one or more biocompatible solvents are present in said plasticizer composition at a concentration of from about 40% v/v to about 10% v/v.

8. The method of claim 7, said soaking is carried out under negative or positive pressure.

9. The method of claim 8, said incubating is carried out under negative pressure.

10. The method of claim 9, said negative pressure is from about 10 to about 50 mBarr for a period of time of from about 18 to about 36 hours.

11. The method of claim 1, said incubating comprising: soaking said cleaned, non-demineralized, load-bearing, bone graft in said one or more plasticizer compositions.

12. The method of claim 1, said incubating comprising: sonicating said cleaned, non-demineralized, load-bearing, bone graft with said one or more plasticizer compositions.

13. The method of claim 1, said incubating comprising: agitating said cleaned, non-demineralized, load-bearing, bone graft with said one or more plasticizer compositions.

14. The method of any one of claims 7, 8, 12, or 13, said incubating is carried out under conditions sufficient to impregnate said bone graft with said one or more plasticizers.

15. The method of any one of claims 7, 8, 12, or 13, said incubating is carried out for a time sufficient to impregnate said bone graft with said one or more plasticizers.

16. A plasticized, non-demineralized load-bearing, bone graft produced by the process as claimed in any one of claims 1, 5, 6, 8, 12, or 13.

17. The method of claim 1, said incubating comprising: centrifuging said cleaned, non-demineralized, load-bearing, bone graft with said one or more plasticizer compositions.

18. The method of claim 17, said centrifuging comprising centrifuging said cleaned, non-demineralized, load-bearing, bone graft with said one or more plasticizer compositions at a speed of from about 2,000 to 3,000 rpm for a time of from about 10 minutes to about 7 hours.

19. The method of claim 18, said speed is about 2,600 rpm and said time is from about 30 minutes to about 5 hours.

20. The method of claim 19, said centrifuging is carried out at a temperature of about 25° C.

21. A method for producing a plasticized, load-bearing, bone graft, comprising;
   subjecting a cleaned, non-demineralized, load-bearing, bone graft with one or more plasticizer compositions comprising one or more plasticizers and one or more biocompatible solvents to negative pressure under conditions sufficient to impregnate said bone graft with said one or more plasticizers.

22. A method for producing a plasticized, load-bearing, bone graft, comprising;
   subjecting a cleaned, non-demineralized, load-bearing, bone graft with one or more plasticizer compositions comprising one or more plasticizers and one more biocompatible solvents to negative pressure of from about 10 to about 50 mBarr for a period of time of from about 18 to about 36 hours, to produce an impregnated bone graft.

23. A method for producing a plasticized, load-bearing, bone graft, comprising:
   centrifuging a cleaned, non-demineralized, load-bearing, bone graft with one or more plasticizer compositions comprising one or more plasticizers and one or more biocompatible solvents, under conditions sufficient to impregnate said bone graft with said one or more plasticizers.

24. A method for producing a plasticized, load-bearing, bone graft, comprising:

centrifuging a cleaned, non-demineralized, load-bearing, bone graft with one or more plasticizer compositions comprising one or more plasticizers and one or more biocompatible solvents, at a speed of from about 2,000 to about 3,000 rpm for a period of time of from about 30 minutes to about 5 hours, to produce an impregnated bone graft.

25. A plasticized, non-demineralized load-bearing, bone graft produced by the process as claimed in any one of claims 21, 22, 23, or 24.

26. The method of any one of claims 22, or 24, further comprising:

removing excess plasticizer from said impregnated bone grafts to produce a plasticized bone graft; and vacuum packaging said plasticized bone graft.

27. The method of claim 26, said removing comprising centrifuging.

28. The method of claim 26, said removing comprising blotting.

* * * * *